(12) United States Patent
Gaulliard et al.

(10) Patent No.: US 6,939,830 B1
(45) Date of Patent: Sep. 6, 2005

(54) METHOD FOR FIGHTING SOIL INSECTS WITH PHENYL-PYRAZOLES

(75) Inventors: Jean-Michel Gaulliard, Montanay (FR); Christian Segaud, Saint Didier au Mont d'Or (FR)

(73) Assignee: Basf Agro B.V. Arnhem (NL) - Wadenswil Branch, Wadenswil (CH)

( * ) Notice: Subject to any disclaimer, the term of this patent is extended or adjusted under 35 U.S.C. 154(b) by 312 days.

(21) Appl. No.: 10/070,457

(22) PCT Filed: Sep. 7, 2000

(86) PCT No.: PCT/FR00/02460

§ 371 (c)(1),
(2), (4) Date: Jul. 19, 2002

(87) PCT Pub. No.: WO01/17354

PCT Pub. Date: Mar. 15, 2001

(30) Foreign Application Priority Data

Sep. 7, 1999 (FR) .............................. 99 11312

(51) Int. Cl.$^7$ ........................ A01N 43/48; A01N 43/56; A61K 31/44
(52) U.S. Cl. ...................... 504/253; 504/280; 504/282; 514/341; 514/403; 514/404
(58) Field of Search .......................... 424/405; 504/253, 504/280, 282; 514/341, 403, 404

(56) References Cited

U.S. PATENT DOCUMENTS

| 4,834,977 | A | 5/1989 | Kohama et al. |
| 5,232,940 | A | 8/1993 | Hatton et al. |

FOREIGN PATENT DOCUMENTS

| EP | 0295117 | | 12/1988 |
| EP | 0836386 B1 | | 8/2001 |
| JP | 08175910 A | * | 7/1996 |
| WO | 87/03781 | | 7/1987 |
| WO | 93/06089 | | 4/1993 |
| WO | 94/21606 | | 9/1994 |
| WO | 97/01278 | | 1/1997 |
| WO | 97/04654 | | 2/1997 |

OTHER PUBLICATIONS

English–language translation of JP 57062201, published Apr. 15, 1982.
English–language translation of JP 01143806, published Jun. 6, 1989.
Database CROPU, STN–International, Acession No. 96–88693 CROPU, XP 002135102, abstract of JP 08 175910, published Jul. 9, 1996, and English translation of JP 08175910.
H.H. Toba et al, Journal of Economic Entomology, vol. 76, No. 4, 1983, pp. 850–855, published by Entomological Society of America, College Park, MD (XP–002135101.
Database CHEMABS, STN–International accession No. 97:87063 (XP 002135103, abstract of JP 57062201, published Apr. 15, 1982.
Database WPI Section Ch, Week 198928, AN 1989–204057 (XP 002135105), abstract of JP 01143806, published Jun. 6, 1989..
Database CABA, accession No. 97:101520, abstract of Chabert et al, STN International, (XP 002135104).

* cited by examiner

Primary Examiner—Alton Pryor
(74) Attorney, Agent, or Firm—Burns, Doane, Swecker & Mathis, L.L.P.

(57) ABSTRACT

The invention concerns insecticide compositions comprising:

(a) between 0.001 and 5%, preferably between 0.05 and 1% of a compound of the type 1-phenyl pyrazole, in particular 1-[2,6-$Cl_2$4-$CF_3$ phenyl]3-CN 4-[SO—$CF_3$] 5-$NH_2$ pyrazole; and (b) between 0.05 and 10%, preferably between 0.1 and 5% of one (or several) moisture retaining agent of the organic type; and (c) between 40 and 99%, preferably between 50 and 98% (and more preferably between 70 and 97%) of vegetable flour.

The invention also concerns a method for fighting insects using said compositions, in particular against click beetles.

49 Claims, No Drawings

METHOD FOR FIGHTING SOIL INSECTS WITH PHENYL-PYRAZOLES

BACKGROUND OF THE INVENTION

A The subject of the present invention is novel compositions intended for controlling soil insects in their various developmental forms, and in particular compositions useful for controlling click beetles. The invention also relates to a method of control using the said compositions.

DESCRIPTION OF RELATED ART

Insecticidal compounds of the phenylpyrazole type which can be used in controlling insects are known in particular from patent applications EP 295117, WO 87/3781, 93/6089 and 94/21606. Patent applications EP 295117 and 836386 also mention compositions comprising from 0.01% to 5% of such active substances.

Click beetles constitute a family of insects which are particularly harmful for certain crops, more particularly for maize, beet, sunflower, potato and rape crops. Their harmful character is all the more marked since the larval forms of click beetles can remain for very long periods in the soil, extending up to 5 years.

Baits have indeed been proposed for various sorts of insects, as well as formulas which can be consumed by ingestion, but these formulas are not necessarily active for all the types of insect and the need remains to find insecticidal forms or formulations which are particularly effective for the most diverse applications, and in particular for controlling click beetles.

In addition, as regards the insecticides applied over or into the soil, it is desirable to find conditions and formulations which make it possible to obtain good efficacy at doses which are as low as possible.

One aim of the invention is to overcome these difficulties completely or in part.

Another aim of the invention is to provide advantageous and effective compositions for controlling non-gregarious insects.

Another aim of the invention is to provide advantageous and effective compositions for controlling soil insects, especially click beetles, and more particularly click beetles in the larval state.

Another aim of the invention is to provide compositions comprising at least one insecticidal active substance of the phenylpyrazole type and which are easily applicable over or into the soil.

Another aim of the invention is to provide insecticide compositions whose performance is good in spite of low applicable doses.

SUMMARY OF THE INVENTION

It has found that these aims could be achieved, completely or in part, by means of the compositions and the control method according to the invention which are described in detail below. It is specified that the percentages indicated in the present text are weight/weight percentages, unless otherwise indicated.

The subject of the present invention is therefore, firstly, insecticidal compositions comprising:

a) between 0.001 and 5%, preferably between 0.05 and 1% and still more advantageously between 0.05 and 0.5% of the compound of formula (I):

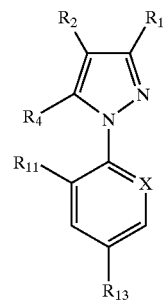

in which:

$R_1$ is a halogen atom or a CN group or a methyl group or a $CH_3CO$ group;

$R_2$ is $S(O)_nR_3$;

$R_3$ is alkyl or haloalkyl;

$R_4$ represents a hydrogen or halogen atom, or an $NR_5R_6$, $S(O)_mR_7$, $C(O)R_7$ or $C(O)O—R_7$, alkyl, haloalkyl or $OR_8$ radical or an $—N=C(R_9)(R_{10})$ radical;

$R_5$ and $R_6$ independently represent a hydrogen atom or an alkyl, haloalkyl, C(O)alkyl or $S(O)_rCF_3$ radical, or $R_5$ and $R_6$ can together form a divalent alkylene radical which may be interrupted by one or two divalent heteroatoms such as oxygen or sulphur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted with one or more halogen atoms or groups such as OH, —O-alkyl, —S-alkyl, cyano or alkyl;

X represents a trivalent nitrogen atom or a $C—R_{12}$ radical, the other three valencies of the carbon atom forming part of the aromatic ring;

$R_{11}$ and $R_{12}$ represent, independently of each other, a hydrogen or halogen atom;

$R_{13}$ represents a halogen atom or a haloalkyl, haloalkoxy, $S(O)_qCF_3$ or $SF_5$ group;

m, n, q, r represent, independently of each other, an integer equal to 0, 1 or 2;

with the proviso that when $R_1$ is methyl, then $R_3$ is haloalkyl, $R_4$ is $NH_2$, $R_{11}$ is Cl, $R_{13}$ is $CF_3$ and X is N;

b) between 0.05 and 10%, preferably between 0.1 and 5% of one (or more) moisture-retaining agents, preferably a moisture-retaining agent of an organic nature; and c) between 40 and 99%, preferably between 50 and 98% (and more preferably between 70 and 97%) of vegetable meal.

The alkyl radicals of the definition of formula (I) generally comprise from 1 to 6 carbon atoms. The ring formed by the divalent alkylene radical representing $R_5$ and $R_6$ as well as by the nitrogen atom to which $R_5$ and $R_6$ are attached is generally a 5-, 6- or 7-membered ring.

DESCRIPTION OF THE PREFERRED EMBODIMENTS

The compound of formula (I) may be prepared according to one of the methods described in patent applications WO 87/3781, 93/6089, 94/21606, EP 295117 or alternatively by another method within the general knowledge of persons skilled in the art competent in chemical synthesis. This compound is generally designated in the present text by the term active substance.

Among the vegetable meals which can be used, there may be mentioned the meals derived from the grinding of cereal grains such as wheat, barley, rye, triticale, oats, or also rice, sorghum, soyabean, maize, the preferred meal being that based on maize. A mixture of these vegetable meals can also be envisaged in the context of the present invention.

Among the moisture-retaining agents of an organic nature, there may be mentioned the macromolecular hydrophilic derivatives of plant origin, and in particular the cellulosic hydrophilic derivatives, and more particularly cellulose, but also one or more disintegrating agents. It may be advantageous to use these compounds in particular when meals such as hard wheat meals are used in the granules. Disintegrating agents include: starch, sodium carboxymethyl starch, cellulose such as microcrystalline cellulose; modified celluloses such as sodium carboxymethylcellulose; bentonite, aluminium and magnesium silicate; sodium polynaphthalenesulphonate, sodium dodecylbenzenesulphonate, sodium dioctylsulphosuccinate, lignin sulphonate; a saccharide derivative such as lactose, fructose, sucrose, mannitol, dextrose; a cross-linked derivative of polyvinylpyrrolidone. When a disintegrating agent is used, the composition according to the invention, may contain from 0.5 to 30%, and preferably from 1 to 20%, by weight of the dry substance, of the said agent(s).

According to a variant of the composition according to the invention, the composition also comprises from 3 to 30%, preferably from 4 to 20% of sugars. The sugars are chosen in particular from mono-, oligo- or polyorganosaccharides, especially from sucrose, lactose, fructose, dextrose, glucose or alternatively molasses or honey.

The compositions which are the subject of the invention may also comprise a preservative preventing the degradation of the meals, such as sodium benzoate, 1,2-benzisothiazolin-3-one, benzoic acid, para-hydroxybenzoic acid and its ester derivatives and its alkali or alkaline-earth metal salts, in particular the sodium salt, 2-phenylphenol and its alkali or alkaline-earth metal salts, in particular the sodium salt, para-nitrophenol.

Other additives may also be included such as colourings or attractants for pests or repellents for birds or animals which are useful or which should be protected.

Other formulation additives may be used such as binding, agglomerating, appetite-enhancing, agglutinating, gelling, swelling or antiadherent agents and the like.

A preferred class of compounds of formula (I) comprises compounds such that $R_1$ is CN, and/or $R_3$ is haloalkyl, and/or $R_4$ is $NH_2$, and/or $R_{11}$ and $R_{12}$ are, independently of each other, a halogen atom, and/or $R_{13}$ is haloalkyl.

According to a particularly advantageous variant of the invention, the compound of formula (I) used in the invention is 5-amino-3-cyano-1-[2,6-di-chloro-4-(trifluoromethyl) phenyl]-4-[(trifluoromethyl)-sulphinyl]-1H-pyrazole, to which reference is made in the examples under the term "fipronil".

The formulations according to the invention are generally in the form of granules. The size of the granules is advantageously between 0.1 mm and 3 cm, preferably between 0.5 and 4 mm. These granules are advantageously insoluble in water (in the sense that they resist disintegration with water). The compositions according to the invention may be prepared by simply mixing the various constituents, preferably by extrusion or compression in the cold or hot state according to any granulation or pelleting technique known per se. For the production of such granules, reference can be easily made to the European patent application published under the number EP 0575838 and/or to other techniques, for example extrusion techniques, known to persons skilled in the art.

The invention also relates to a method of protecting crops from insects, especially click beetles, characterized in that an effective quantity of a composition in the form of granules having a size of between 0.2 mm and 2 cm comprising an active substance chosen from the group consisting of the products of formula I, imidacloprid, acetamiprid, nitenpyram and thiamethoxam, is applied over or into the soil (preferably into the soil) of the area which has to be cultivated.

The invention thus relates more particularly to a method of protecting cereal, preferably maize or beet or sunflower or potato or rape, crops. The application of the formulations according to the invention takes place advantageously before sowing the said crop, or simultaneously with this sowing.

The invention also relates to a method of controlling insects, especially click beetles, characterized in that an effective quantity of one of the compositions according to the invention is applied over or into the soil (preferably into the soil) where they are present or are likely to be present.

As effective quantity, quantities of composition corresponding to a dose of compound of formula (I) of between 1 and 50 g/ha, preferably between 3 and 40 g/ha are often used.

A specific characteristic of the method of controlling insects according to the invention consists in the application, over or into the soil, of a composition providing a dose which is nonlethal through contact but lethal through ingestion.

In other words, in the specific case of click beetles, the method consists in killing the click beetles by application of a dose which is nonlethal through contact but lethal through ingestion. A hypothesis for the good efficacy of the method of treatment according to the invention, which makes it possible to greatly reduce the applicable doses of compounds of formula I in particular, is based on the fact that once the bait according to the invention has caused the death of a click beetle, the latter can itself serve as bait for other click beetles, which therefore also ingest a product (dead click beetle) containing the insecticide.

For the purposes of the present text, the words insecticide and insect should be taken in their broad ordinary-sense and not in their strictly scientific (zoological) sense. Accordingly, the term insect is understood to mean any animal of a very small size such as arthropods (insects in the strict and zoological sense, arachnids, myriapods) and nematodes.

As soil insects against which the invention is particularly effective, there may be mentioned for example:

The *Coleoptera* (wireworms (*Agriotes* spp.), false wireworms, white grubs) such as for example:

*Agriotes lineatus* (European click beetle, Elateridae),

*Agriotes sordidus* (European click beetle, Elateridae),

*Agriotes obscurus* (European click beetle, Elateridae),

*Agriotes sputator* (European click beetle, Elateridae),

*Athous* spp. (Elateridae),

*Atomaria linearis* (Cryptophagidae)

*Melolontha* spp. (white grubs, Scarabaeidae),
*Bothynoderes*
*Limonius* spp. (US click beetle),
*Melanotus* spp. (US click beetle),
*Diabrotica* spp. (cornrootworms, Crysomelidae),
*Tanymecus pallidus* (beet leaf weevil, Curculionidae).

The *Lepidoptera* (Noctuidae) such as:

*Autographa* spp., *Mamestra* spp., *Agrotis* spp. (cutworms, grey grubs), *Euxoa* spp. (cutworms, grey grubs), *Spodoptera* spp. (*Spodoptera exigua, Spodoptera littorlis*).

The *Diptera* such as *Tipula* spp.).

The *Myriapoda* (*Myriapoda*):

*Diplopoda*=Millipedes,

Centipede.

Among the soil click beetles against which the invention is particularly effective, there may be mentioned *Agriotes* spp., *Athous* spp., *Limonius* spp.

The granules according to the invention are advantageously inserted into the soil at a depth of between 1 and 5 cm.

The compositions according to the invention are particularly advantageous in that they allow the use of lower doses of active product than similar known compositions.

The following examples illustrate the invention without however constituting a limitation thereto. In these examples, the compound of formula (I) used is fipronil.

EXAMPLE 1

A surface of 0.1 ha is sown with maize at the rate of about 8000 untreated seeds. This surface is divided into 40-m² plots.

At the same time as the sowing, there are incorporated into the soil, in the sowing row, 2 mm granules containing a composition consisting of:

0.25% of fipronil,
93.5% of maize meal,
2% of cellulose,
4% of lactose,
0.2% of para-nitrophenol,
0.05% of pigment blue 15.3.

The quantities of granules thus spread vary from 2.5 to 10 kg per hectare. Untreated plots are kept to serve as control and to verify the extent of the damage by the insects. Likewise, the plots will be treated with a commercial insecticide which is reputed effective and called reference. Each modality is repeated four times.

Approximately 20 days after sowing, the maize plants which have emerged are counted.

In the locality of St Hilaire (30), 22 days after sowing, 19 plants-are observed in the furrow of the 4 untreated plots per 10 meters of furrow. In the plots treated according to the invention with the dose of fipronil of 6 g per hectare, 49 plants are observed per 10 meters of furrow.

With the dose of fipronil of 12.5 g per hectare, 48 to 50.5 plants are observed per 10 meters of furrow.

With the dose of fipronil of 25 g per hectare, 45.5 to 51.3 plants are observed per 10 meters of furrow.

With the dose of fipronil of 50 g per hectare, 49 plants are observed per 10 meters of furrow.

To obtain the same result with a conventional granule (clay carrier), 200 g of fipronil have to be provided per hectare.

The soil is dug out and scraped in order to capture and identify the insects responsible for the damage; a large presence of larvae of click beetles of the genus *Agriotes*, in particular *Agriotes sordidus*, is observed for the untreated control.

EXAMPLE 2

A surface of 1 ha is sown with maize at the rate of about 98, 100 untreated seeds. This surface is divided into 27-m² plots.

At the same time as the sowing, there are incorporated into the soil, in the sowing row, 2 mm granules containing a composition consisting of:

0.25% of- fipronil,
93.5% of maize meal
2% of cellulose,
4% of lactose,
0.2% of para-nitrophenol,
0.05% of pigment blue 15.3.

The quantities of granules thus spread vary from 2.5 to 10 kg per hectare. Untreated plots are kept to serve as control and to verify the extent of the damage by the insects. Likewise, the plots will be treated with a commercial insecticide which is reputed effective and called reference. Each modality is repeated four times.

Approximately 50 days after sowing, the maize plants which have emerged are counted.

In the locality of Beaufort (62), 50 days after sowing, 30 plants are observed in the furrow of the 4 untreated plots per 10 meters of furrow. In the plots treated according to the invention with the dose of fipronil of 6 g per hectare, 40 plants are observed per 10 meters of furrow.

With the dose of fipronil of 12.5 g per hectare, 43 to 46 plants are observed per 10 meters of furrow.

With the dose of fipronil of 25 g per hectare, 44.5 to 50 plants are observed per 10 meters of furrow.

With the dose of fipronil of 50 g per hectare, 49.8 plants are observed per 10 meters of furrow.

To obtain the same result (52 plants per 10 meters) with a conventional granule (clay carrier), 200 g of fipronil have to be provided per hectare.

The soil is dug out and scraped in order to capture and identify the insects responsible for the damage; a large presence of larvae of click beetles of the genus *Agriotes*, in particular *Agriotes lineatus*.

EXAMPLE 3

Test of efficacy of the bait granules according to the invention on potato crop.

At the same time as the sowing, there are incorporated into the soil, in the sowing row, granules according to the invention consisting of:

12.5 g/kg of fipronil (from an SC containing 500 g/l of fipronil),
945.5 g/kg of a) maize meal (granules A) or b) rice meal (granules B),
40 g/kg of lactose,
2 g/kg of para-nitrophenol.

The efficacy against *Agriotes* (click beetles), 90 days after sowing, of the two granules A and B above, used at the doses of 5 and 2.5 g of fipronil per hectare, and of the same fipronil used by spraying at the doses of 50 and 25 g/ha (from Regent® 800WG) (compound C), was compared.

The following results, expressed as number of holes per 10 tubers (=N) are then observed:

| Product  | A   | A | B   | B | C  | C  | Control* |
|----------|-----|---|-----|---|----|----|----------|
| Dose (g.ha) | 2.5 | 5 | 2.5 | 5 | 25 | 50 | —        |
| N        | 6   | 1 | 7   | 3 | 6  | 1  | 14       |

*untreated control.

This result indeed shows the good control of click beetles which is obtained by the granules according to the invention which give the same result as Regent® 800WG but with a dose reduced by a factor of 10.

What is claimed is:

1. An insecticidal composition comprising:
   (a) between 0.001 and 5% of a compound of formula (I):

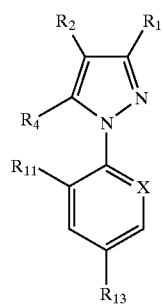

(I)

in which:
R$_1$ is a halogen atom or a CN group or a methyl group or a CH$_3$CO group;
R$_2$ is S(O)$_n$R$_3$;
R$_3$ is alkyl or haloalkyl;
R$_4$ represents a hydrogen or halogen atom, or an NR$_5$R$_6$, S(O)$_m$R$_7$, C(O)R$_7$ or C(O)O—R$_7$, alkyl, haloalkyl or OR$_8$ radical or an —N=C(R$_9$)(R$_{10}$) radical;
R$_5$ and R$_6$ independently represent a hydrogen atom or an alkyl, haloalkyl, C(O)alkyl or S(O)$_r$CF$_3$ radical, or R$_5$ and R$_6$ together form a divalent alkylene radical optionally interrupted by one or two divalent heteroatoms;
R$_7$ represents an alkyl or haloalkyl radical;
R$_8$ represents an alkyl or haloalkyl radical or a hydrogen atom;
R$_9$ represents an alkyl radical or a hydrogen atom;
R$_{10}$ represents a phenyl or heteroaryl group optionally substituted with at least one halogen atom or radical selected from the group consisting of OH, —O-alkyl, —S-alkyl, cyano and alkyl;
X represents a trivalent nitrogen atom or a C—R$_{12}$ radical, the other three valences of the carbon atom forming part of the aromatic ring;
R$_{11}$ and R$_{12}$ represent, independently of each other, a hydrogen or halogen atom;
R$_{13}$ represents a halogen atom or a haloalkyl, haloalkoxy, S(O)$_q$CF$_3$ or SF$_5$ group;
m, n, q, r represent, independently of each other, an integer equal to 0, 1 or 2;
with the proviso that when R$_1$ is methyl, then R$_3$ is haloalkyl, R$_4$ is NH$_2$, R$_{11}$ is Cl, R$_{13}$ is CF$_3$ and X is N;
   (b) between 0.05 and 10% of cellulose as a moisture-retaining agent; and
   (c) between 40 and 99% of at least one vegetable meal.

2. An insecticidal composition according to claim 1, wherein the vegetable meal is derived from the grinding of a cereal grain.

3. An insecticidal composition according to claim 1, wherein the vegetable meal is a maize.

4. An insecticidal composition according to claim 1, wherein the composition also comprises from 3 to 30% of a sugar.

5. An insecticidal composition according to claim 1, wherein the sugar is selected from mono, oligo- or polyorganosaccharides.

6. An insecticidal composition according to claim 1, further comprising a preservative.

7. An insecticidal composition according to claim 1, further comprising one or more additives selected from the group consisting of colorings, attractants for pests, repellents for birds or animals, binding agents, agglomerating agents, appetite-enhancing agents, agglutinating agents, gelling agents, swelling agents and antiadherent agents.

8. An insecticidal composition according to claim 1, wherein the compound of formula (I) is 5-amino-3-cyano-1-[2,6-dichloro-4-(trifluoromethyl)phenyl]-4-[(trifluoromethyl)sulfinyl]-1H-pyrazole.

9. An insecticidal composition according to claim 1, which is in the form of granules of a size between 0.1 mm and 3 cm.

10. An insecticidal composition according to claim 1, wherein the compound of formula (I) is present in an amount of between 0.05 and 1%.

11. An insecticidal composition according to claim 10, wherein the compound of formula (I) is present in an amount of between 0.05 and 0.5%.

12. An insecticidal composition according to claim 1, wherein the moisture-retaining agent is present in an amount of between 0.1 and 5%.

13. An insecticidal composition according to claim 1, wherein the vegetable meal is present in an amount of between 50 and 98%.

14. An insecticidal composition according to claim 13, wherein the vegetable meal is present in an amount of between 70 and 97%.

15. An insecticidal composition according to claim 2, wherein said cereal grain is selected from the group consisting of wheat, barley, rye, triticale, oats, rice, sorghum, soyabean and maize.

16. An insecticidal composition according to claim 4, wherein the sugar is present in an amount of between 4 to 20%.

17. An insecticidal composition according to claim 5, wherein the sugar is sucrose, lactose, fructose, dextrose, glucose, molasses or honey.

18. An insecticidal composition according to claim 6, wherein the preservative is selected from the group consisting of sodium benzoate, 1,2-benzisothiazolin-3-one, benzoic acid, para-hydroxybenzoic acid and its esters and alkali and alkaline-earth metal salts, 2-phenylphenol and its alkali and alkaline-earth metal salts, and para-nitrophenol.

19. An insecticidal composition according to claim 9, wherein the granules are of a size between 0.5 and 4 mm and are water-insoluble.

20. An insecticidal composition according to claim 1, further including from 0.5 to 30% of at least one disintegrating agent.

21. An insecticidal composition according to claim 20, wherein the disintegrating agent is present in an amount of 1 to 20% and is selected from the group consisting of starch, sodium carboxymethyl starch, microcrystalline cellulose, modified celluloses, bentonite, aluminum silicate, magnesium silicate, sodium polynaphthalenesulfonate, sodium dodecylbenzenesulfonate, sodium dioctylsulfosuccinate, lignin sulfonate, a saccharide derivative.

22. A method of controlling insects which comprises applying an effective quantity of an insecticidal composition comprising:

(a) between 0.001 and 5% of a compound of formula (I):

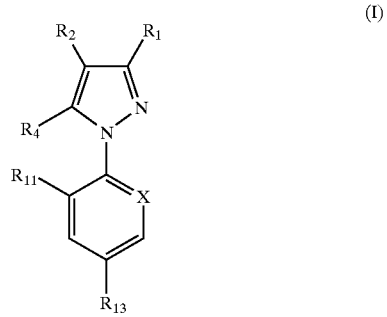

in which:

$R_1$ is a halogen atom or a CN group or a methyl group or a $CH_3CO$ group;

$R_2$ is $S(O)_nR_3$;

$R_3$ is alkyl or haloalkyl;

$R_4$ represents a hydrogen or halogen atom, or an $NR_5R_6$, $S(O)_mR_7$, $C(O)R_7$ or $C(O)O-R_7$, alkyl, haloalkyl or $OR_8$ radical or an $-N=C(R_9)(R_{10})$ radical;

$R_5$ and $R_6$ independently represent a hydrogen atom or an alkyl, haloalkyl, C(O)alkyl or $S(O)_rCF_3$ radical, or $R_5$ and $R_6$ together form a divalent alkylene radical optionally interrupted by one or two divalent heteroatoms;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted with at least one halogen atom or radical selected from the group consisting of OH, —O-alkyl, —S-alkyl, cyano and alkyl;

X represents a trivalent nitrogen atom or a C—$R_{12}$ radical, the other three valences of the carbon atom forming part of the aromatic ring;

$R_{11}$ and $R_{12}$ represent, independently of each other, a hydrogen or halogen atom;

$R_{13}$ represents a halogen atom or a haloalkyl, haloalkoxy, $S(O)_qCF_3$ or $SF_5$ group;

m, n, q, r, represent, independently of each other, an integer equal to 0, 1 or 2;

with the proviso that when $R_1$ is methyl, then $R_3$ is haloalkyl, $R_4$ is $NH_2$, $R_{11}$ is Cl, $R_{13}$ is $CF_3$ and X is N;

(b) between 0.05 and 10% of cellulose as a moisture-retaining agent; and (c) between 40 and 99% of at least one vegetable meal;

in the form of granules having a size of between 0.2 mm and 2 cm over or into the soil in an area which is to be cultivated.

23. A method according to claim 22, wherein the effective quantity is selected to provide a dosage which is nonlethal through contact but lethal through ingestion.

24. A method according to claim 22, wherein the insect being controlled is a click beetle.

25. A method according to claim 22, wherein the effective quantity is between 1 and 50 g/ha.

26. A method according to claim 25, wherein the effective quantity is between 3 and 40 g/ha.

27. A method according to claim 22, wherein the vegetable meal is maize.

28. A method according to claim 22, wherein the composition also comprises from 3 to 30% of a sugar and from 0.5 to 30% of at least one disintegrating agent.

29. A method according to claim 28, wherein the sugar is lactose and the disintegrating agent is lactose.

30. A method according to claim 22, wherein the compound of formula (I) is 5-amino-3-cyano-1-[2,6-dichloro-4-(trifluoromethyl)phenyl]-4-[(trifluoromethyl)sulfinyl]-1H-pyrazole.

31. A method according to claim 30, wherein the vegetable meal is maize and the composition also comprises from 3 to 30% of a sugar and from 0.5 to 30% of at least one disintegrating agent.

32. A method according to claim 31, wherein the sugar is lactose and the disintegrating agent is lactose.

33. A method of protecting crops which comprises applying over or into the soil before or simultaneously with sowing the crops, an effective amount of an insecticidal composition comprising:

(a) between 0.001 and 5% of a compound of formula (I):

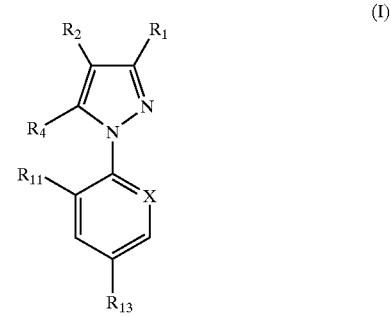

in which;

$R_1$ is a halogen atom or a CN group or a methyl group or a $CH_3CO$ group;

$R_2$ is $S(O)_nR_3$;

$R_3$ is alkyl or haloalkyl;

$R_4$ represents a hydrogen or halogen atom, or an $NR_5R_6$, $S(O)_mR_7$, $C(O)R_7$ or $C(O)O-R_7$, alkyl, haloalkyl or $OR_8$ radical or an $-N=C(R_9)(R_{10})$ radical;

$R_5$ and $R_6$ independently represent a hydrogen atom or an alkyl, haloalkyl, C(O)alkyl or $S(O)_rCF_3$ radical, or $R_5$ and $R_6$ together form a divalent alkylene radical optionally interrupted by one or two divalent heteroatoms;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted with at least one halogen atom or radical selected from the group consisting of OH, —O-alkyl, —S-alkyl, cyano and alkyl;

X represents a trivalent nitrogen atom or a C—$R_{12}$ radical, the other three valences of the carbon atom forming part of the aromatic ring;

$R_{11}$ and $R_{12}$ represent, independently of each other, a hydrogen or halogen atom;

$R_{13}$ represents a halogen atom or a haloalkyl, haloalkoxy, $S(O)_q CF_3$ or $SF_5$ group;

m, n, q, r represent, independently of each other, an integer equal to 0.1 or 2;

with the proviso that when $R_1$ is methyl, then $R_3$ is haloalkyl, $R_4$ is $NH_2$, $R_{11}$ is Cl, $R_{13}$ is $CF_3$ and X is N;

(b) between 0.05 and 10% of cellulose as a moisture-retaining agent; and (c) between 40 and 99% of at least one vegetable meal; in the form of granules.

34. A method according to claim 33, wherein the crop to be protected is a cereal, beet, sunflower, potato or rape.

35. A method according to claim 33, wherein the effective amount comprises between 1 and 50 g/ha.

36. A method according to claim 35, wherein the amount is between 3 and 40 g/ha.

37. A method according to claim 34, wherein the vegetable meal is maize.

38. A method according to claim 34, wherein the composition also comprises from 3 to 30% of a sugar and from 0.5 to 30% of at least one disintegrating agent.

39. A method according to claim 38, wherein the sugar is lactose and the disintegrating agent is lactose.

40. A method according to claim 33, wherein the compound of formula (I) is 5amino-3-cyano-1-[2,6-dichloro-4-(trifluoromethyl)phenyl]-4-[(trifluoromethyl)sulfinyl)]-1H-pyrazole.

41. A method according to claim 40, wherein the vegetable meal is maize and the composition also comprises from 3 to 30% of a sugar and from 0.5 to 30% of at least one disintegrating agent.

42. A method according to claim 41, wherein the sugar is lactose and the disintegrating agent is lactose.

43. An insecticidal composition comprising;

(a) between 0.001 and 5% of the compound 5-amino-3-cyano-1-[2,6-dichloro-4-(trifluoromethyl)phenyl]-4-[(trifluoromethyl)sulfinyl]-1H-pyrazole;

(b) between 0.05 and 10% of cellulose as a moisture-retaining agent; and (c) between 40 and 99% of at least one vegetable meal.

44. An insecticidal composition according to claim 43, wherein the vegetable meal is maize.

45. An insecticidal composition according to claim 43, wherein the composition also comprises from 3 to 30% of a sugar and from 0.5 to 30% of at least one disintegrating agent.

46. An insecticidal composition according to claim 45, wherein the vegetable meal is maize.

47. An insecticidal composition according to claim 45, wherein the sugar is lactose and wherein the disintegrating agent is lactose.

48. An insecticidal composition according to claim 47, wherein the vegetable meal is maize.

49. A method of controlling insects which comprises applying an effective quantity of an insecticidal composition comprising:

(a) between 0.001 and 5% of the compound 5-amino-3-cyano-1-[2,6-dichloro-4-(trifluoromethyl)phenyl]-4-[(trifluoromethyl)sulfinyl]-1H-pyrazole;

(b) between 0.05 and 10% of cellulose as a moisture-retaining agent; and (c) between 40 and 99% of at least one vegetable meal;

in the form of granules having a size of between 0.2 mm and 2 cm over or into the soil in an area which is to be cultivated.

\* \* \* \* \*

UNITED STATES PATENT AND TRADEMARK OFFICE
CERTIFICATE OF CORRECTION

PATENT NO. : 6,939,830 B1
DATED : September 6, 2005
INVENTOR(S) : Jean-Michel Gaulliard and Christian Segaud It is certified that error appears in the above-identified patent and that said Letters Patent is hereby corrected as shown below:

Column 8,
Line 9, should read -- An insecticidal composition according to claim 4, wherein --.

Column 9,
Line 5, should read -- lignin sulfonate, and a saccharide derivative. --.

Column 11,
Lines 20 and 22, should read -- A method according to claim 33, wherein --.
Line 28, should read -- pound of formula (I) is 5-amino-3-cyano-1-[2,6-dichloro-4- --.

Signed and Sealed this

Seventh Day of February, 2006

JON W. DUDAS
*Director of the United States Patent and Trademark Office*